US007097862B2

(12) United States Patent
Hodge

(10) Patent No.: US 7,097,862 B2
(45) Date of Patent: Aug. 29, 2006

(54) METHODS OF INHIBITING TUMOR NECROSIS FACTOR

(76) Inventor: Thomas W. Hodge, 9115 Twelvestone Dr., Roswell, GA (US) 30076

( * ) Notice: Subject to any disclaimer, the term of this patent is extended or adjusted under 35 U.S.C. 154(b) by 0 days.

(21) Appl. No.: 10/255,915

(22) Filed: Sep. 26, 2002

(65) Prior Publication Data

US 2003/0108571 A1 Jun. 12, 2003

Related U.S. Application Data

(63) Continuation of application No. 09/758,296, filed on Jan. 10, 2001, now abandoned, which is a continuation of application No. 08/823,985, filed on Mar. 25, 1997, now abandoned, which is a continuation of application No. 08/611,939, filed on Mar. 6, 1996, now abandoned, which is a continuation of application No. 08/447,721, filed on May 23, 1995, now abandoned, which is a continuation of application No. 08/168,661, filed on Dec. 16, 1993, now abandoned, which is a continuation-in-part of application No. 07/953,051, filed on Sep. 30, 1992, now abandoned, which is a continuation-in-part of application No. 07/953,052, filed on Sep. 30, 1992, now abandoned, which is a continuation-in-part of application No. 08/063,218, filed on May 17, 1993, now abandoned.

(51) Int. Cl.
*A61K 35/78* (2006.01)

(52) U.S. Cl. ...................................................... 424/725

(58) Field of Classification Search ................. 424/725
See application file for complete search history.

(56) References Cited

U.S. PATENT DOCUMENTS

| | | | |
|---|---|---|---|
| 3,679,893 | A | 7/1972 | Cook et al. |
| 3,992,364 | A | 11/1976 | Kuhlmey |
| 4,684,740 | A | 8/1987 | Higuchi et al. |
| 5,180,588 | A | 1/1993 | Shinmen et al. |
| 5,211,953 | A | 5/1993 | Shinmen et al. |
| 5,215,743 | A | 6/1993 | Singh et al. |
| 5,288,852 | A | 2/1994 | Yamada et al. |

FOREIGN PATENT DOCUMENTS

| | | |
|---|---|---|
| EP | 0140134 | 5/1985 |
| GB | 1142571 | 2/1969 |
| JP | 62-167791 | 8/1993 |

OTHER PUBLICATIONS

Brown, Health Store News, Oct./Nov. 1991.*

Brown, Townsend Letter for Doctors, Jul. 1991, pp. 597-598.*

PCM-4 Package Label, Omega.*

"The Merck Manual of Diagnosis and Therapy" Merck Research Laboratories, Rahway, NJ Sixteenth Edition, 1992.

Hirano, et al. "Suppression of mitogen-induced proliferation of human peripheral blood lymphocytes by plant lignans", Planta Med 57(4): 331-4, 1991.

Oshima, et al., "Anticomplementary Activity of the Constituents of Eucommia Ulmoides Bark", J.Ethnopharmacology 23:159-164, 1988.

Wagner, et al, "Studies on the Standardization of Mistletoe Preparations", Oncology 43: Suppl 1:16-22, 1986.

Bohn et al. "Flow-cytometric Studies with *Eleutherococcus senticosus* Extract as an Immunomodulatory Agent" Arzneim-Forsch/Drug Res 37(II) No. 10 1193-1196, 1987.

Donald J. Brown, "Phytotherapy Review & Commentary", Townsend Letter for Doctors. Aug./Sep. 1991.

Donald J. Brown, "Phytotherapy Review & Commentary", Townsend Letter for Doctors, Jul. 1991, p. 597.

Lark Lands, Ph.D., "Drug Information for People Living with HIV", HIV Treatment Strategy, Part III, Jun. 1991.

"The Drug that Builds Russians", New Scientist, Aug. 21, 1980, pp. 576-579.

Excerpted from "Eleutherococcus: Strategy of the Use and New Fundamental Data", Barenboim, G.M., Kozlova, N.B.

Weger, "Preparation and Chemistry of *Eleutherococcus senticosus* Maxim.", Sep. 20, 19990.

Baier, et al., Improvement of Impaired Mitogen-Induced Interferon-Gamma Release of Peripheral Blood Mononuclear Cells Derived from Tumor Patients by "P"., Abstract from Onkologie: Internationale Zeitschrift fuer Krebsforschung und-Behandlung, 1991; 14; Supplement 2;7.

Autoimmunity and Autoimmune Diseases, p. 821.

Duesberg, AIDS epidemiology: Inconsistencies with . . . virus and with infectious disease:, Proc. Natl. Acad. Sci.—USA, 88:1575-1579 (1991).

Duesberg, et al., "Is the AIDS Virus a Science Fiction?", Policy Review. pp. 40-51.

Root-Bernstein, "AIDS is More than HIV: Part I", Genetic Engineering News, Sep. 1, 1992, pp. 4-6.

"PCM-4 product label."

Andrew Pelter, et al., Synthesis of 2.6 Diaryl-4, 8-dihydroxy-3, 7-dioxabicyclo {3.3.0.} ictaubesim Journal of the Chemical Society, vol. 1:175-181 (Jan. 1982).

Oshima, et al., "Anticomplementary Activity of the Constituents of Eucommia Ulmoides Bark", Journal of Ethnopharmacology, 23 (1988) pp. 159-164.

(Continued)

*Primary Examiner*—Jean C. Witz
(74) *Attorney, Agent, or Firm*—Bradley Arant Rose & White LLP

(57) ABSTRACT

The disclosure describes a method of inhibiting TNF in subjects comprising administering a TNF inhibiting amount of an extract of *Eleutherococcus senticosus maxim* to a subject. In addition, the present disclosure provides a method of inhibiting TNF in a cell line comprising administering to the cell line a TNF inhibiting amount of an extract from *Eleutherococcus senticosus maxim*. Finally, the disclosure provides a method of treating a TNF mediated disorder in a subject, comprising administering an effective amount of an extract of *Eleutherococcus senticosus maxim* to the subject.

4 Claims, 1 Drawing Sheet

OTHER PUBLICATIONS

Hirano, et al., 115 CA 174084p (1991).
Starosel'skii, et al. (1991) Vopr Onkol, (37) pp. 875-877 (Abstract).
Kamaukh, et al. (1990) Vrach Delo (10), pp. 119-121.
Domashenko, et al., (1989) Lab Delo (5), pp. 15-17.
Chubarev, et al. (1989) Farmakol Toksikol 52, pp. 55-59 (Abstract).
Strel'chuk, (1987) Tsitol Genet, 21 (2) pp. 136-139 (Abstract).
Gubar', et al., (1993) Biotechnology, 3 pp. 28-31 (Abstract).
Molokoviskii, et al., (1989) Probl Endokrinol (Mosk), 35 (6) pp. 82-87.
Medline Abstract accession No.: 93097542.
Medline Abstract accession No.: 86291252.
"PCM-4 package insert", (1991).
"PCM-4 promotional literature", (1991).
Van De Graaff, et al., Concepts of Human Anatomy and Pysiology, (1986) Glossary, Wm.C. Brown Publishers, Dubuque, Iowa.
Donald J. Brown, "PCM-4: New Standard of Excellence in Immunomodulation", Health Store News (Nov. 1992).

* cited by examiner

METHODS OF INHIBITING TUMOR NECROSIS FACTOR

This application is a continuation of, and claims the benefit of, application Ser. No. 09/758,296 filed Jan. 10, 2001, now abandoned which is a continuation of Ser. No. 08/823,985, filed Mar. 25, 1997 (now abandoned), which is a continuation of Ser. No. 08/611,939, filed Mar. 6, 1996 (now abandoned), which is a continuation of Ser. No. 08/447,721, filed May 23, 1995 (now abandoned), which is a continuation of Ser. No. 08/168,661, filed Dec. 16, 1993 (now abandoned), which is a continuation-in-part of Ser. No. 07/953,051, filed Sep. 30, 1992 (now abandoned), Ser. No. 07/953,052, filed Sep. 30, 1992 (now abandoned), and Ser. No. 08/063,218, filed May 17, 1993 (now abandoned), the contents of each of which are hereby incorporated by this reference.

FIELD OF THE DISCLOSURE

This disclosure relates to the use of *Eleutherococcus senticosus maxim* extract to inhibit tumor necrosis factor (TNF) in subjects, including humans, animals and cell lines thereof, and to treat disorders mediated by TNF in subjects.

BACKGROUND

It is becoming increasingly evident that tumor necrosis factor (TNF) is a cytokine involved in numerous pathologies afflicting subjects, including animals and humans. For-instance, introduction of the endotoxin from gram(−) bacteria induces the production of cytokines including TNF. Excessive production of such cytokines is thought to be the cause of endotoxic or septic shock. In addition, TNF has been shown to activate latent HIV infected cells in vitro and in vivo. (See Zinnser, *Microbiology,* 20th Ed. Appleton & Lange, 1992, at p. 1052.)

A crude extract derived from the root of *Eleutherococcus senticosus maxim* (*E. maxim*) has been utilized to treat various disorders. This *Eleutherococcus senticosus maxim* root extract is marketed under the name CM-4™ (trademark of Omega Pharmaceutical, Inc. for an *Eleutherococcus senticosus maxim* extract as described at page 5 herein). In addition, *Eleutherococcus senticosus maxim* extract has been marketed in combination with a spleen extract as PCM-4™ (trademark of Omega Pharmaceutical, Inc. for a product containing, as one ingredient, CM-4™ as wells as a mixture of polypeptides).

*Eleutherococcus senticosus maxim* extract has been used treat anemia, depression, diseases of the heart and blood vessels, the rigors of surgery, convalescence, tuberculosis, and aging. PCM-4™ has also been used to treat HIV+ patients. However, despite the many therapeutic benefits associated with *Eleutherococcus senticosus maxim* extract, additional properties of this extract are continually being found which are of great value to mankind. The present application provides the surprising discovery and use of *Eleutherococcus senticosus maxim* extract as an inhibitor of tumor necrosis factor (TNF).

SUMMARY

The present disclosure provides a method of inhibiting TNF in a subject comprising administering to the subject a TNF inhibiting amount of an extract from *Eleutherococcus senticosus maxim*. Suitable subjects include humans and animals. The *Eleutherococcus senticosus maxim* extract inhibits both TNF-α and TNF-β.

In addition, the present disclosure provides a method inhibiting TNF in a cell comprising administering to the cell a TNF inhibiting amount of an extract from *Eleutherococcus senticosus maxim*. Suitable subjects include humans and animals and cell lines derived there from. *Eleutherococcus senticosus maxim* extract inhibits both TNF-α and TNF-β.

Finally, the present disclosure provides a method of treating a TNF mediated disorder in a subject, comprising administering a therapeutic amount of an extract of *Eleutherococcus senticosus maxim* to the subject. Suitable subjects include humans and animals. The *Eleutherococcus senticosus maxim* extract treats disorders mediated by both TNF-α and TNF-β.

DETAILED DESCRIPTION

Figure 1:
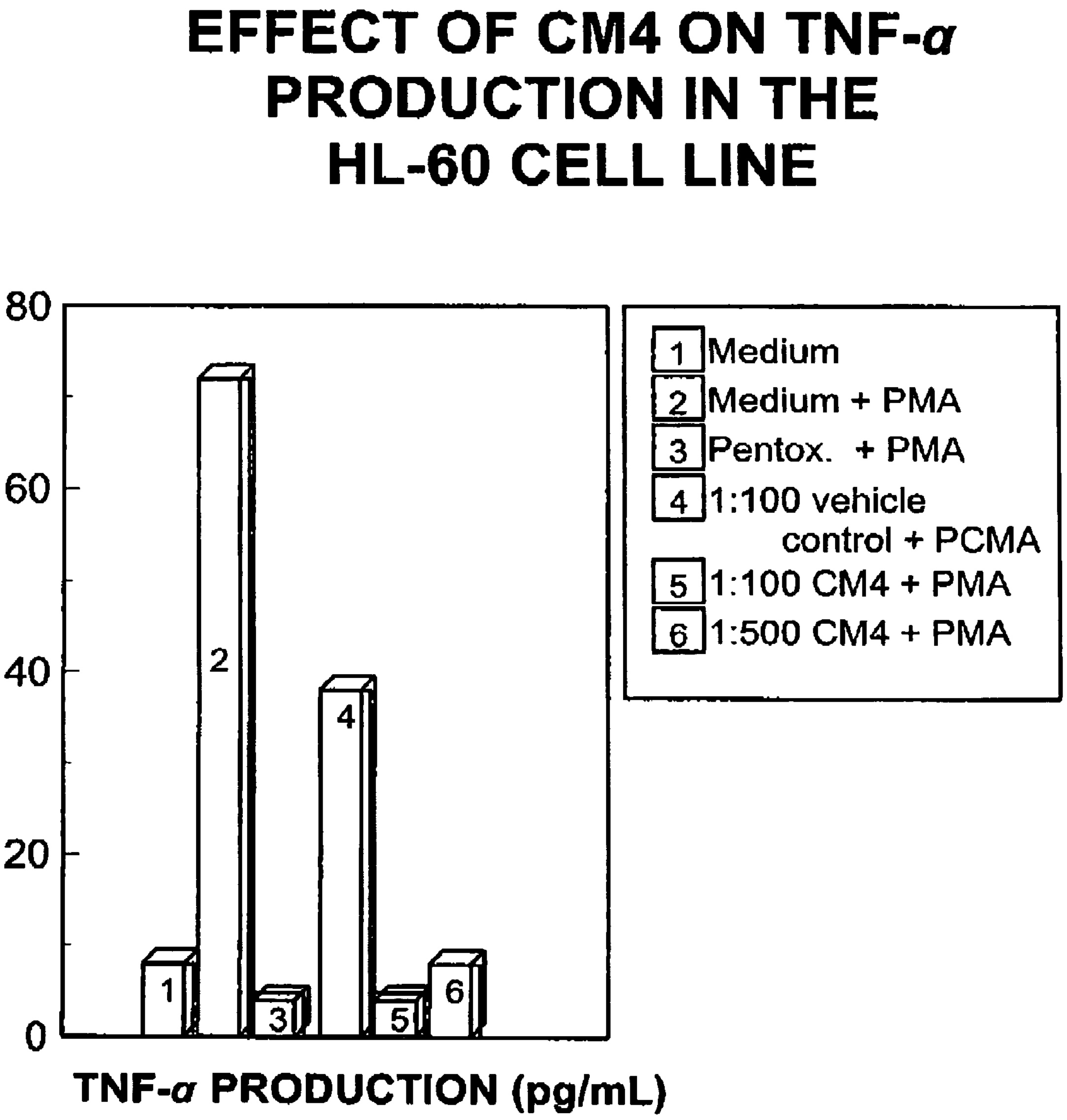
FIG. 1 shows the effect of *Eleutherococcus senticosus maxim* extract on TNF production in the HL-60 cell line.

The present disclosure provides a method of inhibiting TNF in a subject and in a cell comprising administering to the subject or cell line a TNF inhibiting amount of an extract from *Eleutherococcus senticosus maxim*. The method of the invention may be practiced upon subjects including humans. The *Eleutherococcus senticosus maxim* extract of the invention inhibits both TNF-α and TNF-β. In one embodiment the extract is CM-4™. In an alternate embodiment the extract is PCM-4™.

Furthermore, the present disclosure provides a method of treating a TNF mediated disorder in a subject, comprising-administering a therapeutic amount of an extract of *Eleutherococcus senticosus maxim* to the subject. Suitable subjects include humans and animals. The *Eleutherococcus senticosus maxim* extract treats disorders mediated by both TNF-α and TNF-β. In one embodiment the extract is CM-4™. In an alternate embodiment the extract is PCM-4™.

Inhibition and mediation can occur through both prevention of cellular production of TNF and through competitive antagonism or other incapacitation of extant TNF in the subject or cell line. Since the *Eleutherococcus senticosus maxim* is a TNF inhibitor, the pathologies treated will be the result of TNF mediated harm. Typically, such TNF mediated harm will be the result of an overproduction of TNF. Examples of TNF mediated pathologies included, but are not limited to, toxic shock, cancer, chronic diarrhea and wasting syndrome. Wasting syndrome is a common problem among HIV-infected people and the elderly population. Wasting syndrome is defined as unintended and progressive weight loss often accompanied by weakness, fever, nutritional deficiencies and chronic diarrhea. The syndrome, also known as cachexia, can diminish the quality of life, exacerbate illness and increase the risk of death for people with HIV. Researchers also have found that increased levels of immune-signaling molecules (cytokines) such as TNF-α are associated with wasting, specifically HIV-induced wasting. Drugs that block TNF-α are predicted to have a role in the treatment of this condition. In one embodiment the extract is CM-4™. In an alternate embodiment the extract is PCM-4™.

Definitions and Nomenclature:

It is to be understood that this disclosure is not limited to specific synthetic methods, specific pharmaceutical carriers, or to particular pharmaceutical formulations or administration regimens, as such may, of course, vary. It is also to be understood that the terminology used herein is for the purpose of describing particular embodiments only and is not intended to be limiting.

It must be noted that, as used in the specification and the appended claims, the singular forms “a,” “an” and “the” can include plural-referents unless the context clearly dictates otherwise. Thus, for example, reference to “a compound” includes mixtures of compounds, reference to “a pharmaceutical carrier” includes mixtures of two or more such carriers, and the like.

For the purposes of this disclosure, the term “inhibiting” as it relates to levels of TNF in subjects and cell lines refers to both the prevention of production of TNF in the respective subjects or cell lines and also to prevention of the activity of any TNF which already is present in the subject or cell line. For example, inhibition of TNF can refer to the ability of CM-4™ to prevent cellular production of TNF as in Example I with the HL-60 cell line. In addition, as shown in Example II below, inhibition of TNF can also refer to the ability of CM-4™ to reduce the deleterious effects of existing TNF levels. Thus, in Example II, CM-4™ was able to significantly reduce reverse transcriptase activity (i.e. viral replication) in OM-10.1 cells despite the presence of levels of TNF sufficient to stimulate viral replication.

By the term “TNF inhibiting amount” or an “effective amount” of a composition as provided herein is meant a nontoxic but sufficient amount of the TNF inhibiting composition to provide the desired activity. As will be pointed out below, the exact amount required will vary from subject to subject, depending on the species, age, and general condition of the subject, the severity of the disease that is being treated, the particular compound used, its mode of administration, and the like. Thus, it is not possible to specify an exact “TNF inhibiting amount.” However, an appropriate TNF inhibiting amount may be determined by one of ordinary skill in the art using only routine experimentation.

The *Eleutherococcus senticosus maxim* extract can exist in pharmaceutically acceptable carriers. A “pharmaceutically acceptable” material is one that is not biologically or otherwise undesirable, i.e., a material that may be administered to an individual along with the selected composition without causing any undesirable biological effects or interacting in a deleterious mangier with any of the other components of the pharmaceutical composition in which it is contained. One example of the extract in a suitable carrier is CM-4™ as described below.

It must also be understood that the term ‘subjects’ as used herein is meant to include animals including humans. In addition, the dilutions of *Eleutherococcus* extracts are meant to be dilutions in cell culture medium or other neutral carrier. For example, a 1:300 dilution includes 1 part *Eleutherococcus* extract to 300 parts cell culture medium. By “extract” it is meant an active composition obtained from *Eleutherococcus senticosus maxim* wherein the *Eleutherococcus* root is a primary component either in solid, liquid, paste or the like.

Extract Preparation:

Extracts can be obtained by various methods. One extract, CM-4™, is a protic extract of that *Eleutherococcus* root in an ethanol-water extract. PCM-4™ contains the CM-4™ protic extract as one of its components.

The preferred process for preparing *Eleutherococcus senticosus maxim* extract is as follows. *Eleutherococcus senticosus maxim* root is extracted, shaken free of dirt and sand, and washed with cold flowing water. The root is then dried by baking for one hour at 80° C. After baking, the roots are allowed to continue drying in a vacuum drier at 60° C. or in a warm, dry and well-ventilated location. Then roots are selected based on the following criteria: 1) the root is whole or in small parts, the bark on the outside is a yellow-brown color and internally the root is white, 2) the outside bark of the root is wrinkled, indicating that it has dried properly, 3) breaking the root open reveals a white, slightly fibrous, strongly scented aromatic characteristic odor, and 4) the taste is of the root is spicy and slightly bitter.

The selected roots are then ground into a medium-coarse powder. This powder is mixed with a protic solvent such as 40% ethanol (60% water) by volume for the extraction (1 kg powder per liter of 40% ethanol) and the mixture is heated (Pharmacopeia of USSR, page 522). The extraction can be accomplished with other protic solutions, such as water or alcohol-water solutions, for example 10–100% ethanol solutions with water.

The resulting extract is a darkish brown fluid of a specific color, is transparent, and is bitter. This extract has a dry residue of not less than 6% (Pharmacopeia, supra, p. 253), and an alcohol content of not less than 33% (Pharmacopeia, supra, p. 813).

Administration:

The *Eleutherococcus senticosus maxim* extract of the disclosure may be conveniently formulated into various pharmaceutical compositions composed of *Eleutherococcus senticosus maxim* extract in association with a pharmaceutically acceptable carrier. *Remington's Pharmaceutical Sciences*, latest edition, by E. W. Martin (Mack Publ. Co., Easton Pa.) (which is incorporated by reference herein) discloses typical carriers and conventional methods of preparing pharmaceutical compositions that may be used in conjunction with the preparation of formulations.

Depending on the intended mode of administration, the pharmaceutical compositions may be in the form of solid, semi-solid or liquid dosage forms, such as, for example, tablets, suppositories, pills, capsules, powders, liquids, suspensions, lotions, creams, gels, or the like, preferably in unit dosage form suitable for single administration of a precise dosage. The compositions will include, as noted above, an effective amount of *Eleutherococcus senticosus maxim* extract in combination with a pharmaceutically acceptable carrier and, in addition, may include other medicinal agents, pharmaceutical agents, carriers, adjuvants, diluents, etc.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc., *Eleutherococcus senticosus maxim* extract as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences*, referenced above.

For oral administration, fine powders or granules may contain diluting, dispersing, and/or surface active agents, and may be presented in water or in a syrup, in capsules or sachets in the dry state, or in a nonaqueous solution or suspension wherein suspending agents may be included, in tablets wherein binders and lubricants may be included, or in a suspension in water or a syrup. Where desirable or necessary, flavoring, preserving, suspending, thickening, or emulsifying agents may be included. Tablets and granules are preferred oral administration forms, and these may be coated.

Parenteral administration, if used, is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system, such that a constant level of dosage is maintained. See, e.g., U.S. Pat. No. 3,710,795, which is incorporated by reference herein.

In one embodiment, the *Eleutherococcus senticosus maxim* extract can be administered on a daily basis to a subject, in an amount equivalent to about 0.5–7 ml of an about 27.5% by volume ethanol in water extract of *Eleutherococcus*. Such administration can be in any pharmaceutical composition described above, or a combination thereof. In alternate embodiments of administration to a subject, an equivalent of about 3.3 ml of *Eleutherococcus senticosus maxim* extract is administered to the subject on a daily basis. Such administration can be in any pharmaceutical composition described above, or a combination thereof. The *Eleutherococcus senticosus maxim* extract can be taken as a single dose daily, or in multiple doses daily. Alternatively, an extract is administered to the subject before breakfast daily, and an equivalent of about 1.1 ml of *Eleutherococcus senticosus maxim* extract is administered to the subject daily at lunch.

Experimental

The following examples are put forth so as to provide those of ordinary skill in the art with a complete disclosure and description of how the *Eleutherococcus senticosus maxim* extract used in the methods claimed herein is made and evaluated, and are not intended to limit the scope of the disclosure. Efforts have been made to ensure accuracy with respect to numbers (e.g., amounts, temperature, etc.) but some errors and deviations should be accounted for.

EXAMPLE I

HL-60

HL-60 cells are a human leukemia cell line known to produce high levels of TNF in response to Phorbol myristate acetate (PMA). In order to assay the effects of *Eleutherococcus senticosis maxim* extract on HL-60, HL-60 cells ($2\times10^6$) in supplemented RPMI-1640 medium were incubated four hours in the presence of various dilutions of extract, in this case CM-4™. PMA was added and the incubation continued at 37° C. in 95% air 5% $CO_2$. TNF production was determined by ELISA. Controls were cells alone, cells with 33% ethanol, and cells with pentoxaphyllin. The results are detailed in FIG. 1.

The results in FIG. 1 show the effect of CM-4™ on TNF production in the HL-60 cell line. Specifically, HL60 showed a marked decrease in TNF production upon treatment with 1:100 dilution of CM-4™ and 1:500 dilution of CM4™. At the 1:100 dilution TNF production was less than 5 pg/ml whereas the control registered about 70 pg/ml. At 1:500, CM-4™ limited TNF production to less than 10 pg/ml (see FIG. 1). In addition, addition of pentoxaphyllin resulted in very little TNF production (<5 pg/ml). Therefore, CM-4™ in dilutions from about 1:100 to 1:500 proved to be highly effective in inhibiting TNF production in HL-60 cells.

EXAMPLE II

OM 10.1

OM 10.1 is a derivative of the HL-60 cell line that is latently infected with HIV-1. In response to TNF-α, HIV-1 is induced to produce viral particles.

The OM 10.1 cell line, stock cultures, obtained from the AIDS Research and Reference Reagent Program, MAID, were subjected to 2 passages in the presence of 5 μ/ml AZT prior to use in order to decrease background p24 and reverse transcriptase (RT) levels due to superinfection. The cells thus prepared demonstrated increased p24 and RT levels when subjected to stimulation with TNF-α with a concomitant decrease in CD4 expression as measured by FACS analysis following incubation with OK T4 antibody (Becton-Dickenson).

For experimental use, OM 10.1 cells were harvested from a stock culture and washed by centrifugation with Dulbecco's phosphate-buffered saline. The cells were resuspended in cell culture medium (RPMI 1640 medium) containing 10% fetal bovine serum (heat-inactivated at 56° C. for 30 minutes, 100 IU/ml penicillin, 100 μg/ml streptomycin, 20 μg/ml gentamicin, 8 μg/ml tylosin, and 25 mM HEPES). The cultures were maintained in a humidified atmosphere of 5% $CO_2$ in disposable plastic cell cultureware. The cells were seeded at 800,000 cells/2ml/well in six well plates and an equal volume of drug dilution in cell culture medium was added.

Following 1 hour of incubation, 20 U/ml of TNF-α was added to appropriate wells. Culture fluids were harvested after 48 hours of incubation for determination of RT activity and p24 content. Standard methods were used in the RT assays and in the ELISA assays for HIV p24 antigen. The results of this assay are summarized in Table 1.

Table 1 shows the effect of varying concentrations of CM-4™ on HIV replication by inhibition of TNF-α in latently infected cells. The data indicate that at dilutions of from about 1:300 to 1:600, the CM-4™ extract is not toxic to the subject cells. Furthermore, the data indicate that reverse transcriptase activity is significantly inhibited in OM 10.1 cells by the addition of the CM-4™ extract when TNF-α is present. Therefore, the CM-4™ extract was effective in preventing stimulation of virus production/replication when administered at non-cytotoxic levels.

TABLE 1

Evaluation of *Eleutherococcus senticosus maxim* extract for Inhibition of the Stimulation by TNF-α of Active Virus Production in OM 10.1 Cells Latently Infected with HIV

| TNF-α | CM-4 ™$^A$ | CPM (RT)$^B$ | Viability$^C$ | Cytotoxicity | % S$^D$ | % I$^E$ |
|---|---|---|---|---|---|---|
| – | – | 10804 | — | — | — | — |
| – | 1:200 | 5157 | 70% | Toxic | — | — |
| – | 1:300 | 13324 | 92% | Non-toxic | 2 | — |
| – | 1:400 | 12231 | 92% | Non-toxic | 1 | — |
| | 1:600 | 20027 | 96% | Non-toxic | 7 | — |

TABLE 1-continued

Evaluation of *Eleutherococcus senticosus maxim* extract for Inhibition of the Stimulation by TNF-α of Active Virus Production in OM 10.1 Cells Latently Infected with HIV

| TNF-α | CM-4 ™[A] | CPM (RT)[B] | Viability[C] | Cytotoxicity | % S[D] | % I[E] |
|---|---|---|---|---|---|---|
| + | – | 148547 | — | — | — | — |
| + | 1:200 | 9125 | 62% | Toxic | — | — |
| + | 1:300 | 31770 | 87% | Non-toxic | — | 85 |
| + | 1:400 | 58825 | 84% | Non-toxic | — | 65 |
| + | 1:600 | 91779 | 95% | Non-toxic | — | 42 |

[A]Refers to the final concentration (dilution).
[B]RT is used as the abbreviation for reverse transcriptase activity which is measured by standard methods. CPM is counts per minute of radioactivity.
[C]Viability was measured by trypan blue exclusion hemacytometer cell counts.
[D]% S is the stimulation of reverse transcriptase activity seen in relation to that produced by TNF-α. *The Eleutherococcus senticosus maxim* extract preparation did not produce significant stimulation of virus production.
[E]% I is the inhibition of TNF-α stimulated RT activity seen in the presence of *Eleutherococcus senticosus maxim* extract. *Eleutherococcus senticosus maxim* extract was effective in preventing the stimulation of virus at non-cytotoxic concentrations.

What is claimed:

1. A method of inhibiting TNF in a cell line in need of said inhibiting, the method comprising administering to the cell line a TNF inhibiting amount of a protic alcohol water extract from the roots of *Eleutherococcus senticosus maxim*, said roots being dried, ground to a course powder and mixed with said protic extract such that the resulting extract has a dark brown color, has a dry residue of not less than 6% and has an alcohol content of not less than 33%.

2. The method of claim 1 where the TNF is at least one of the TNF selected from the group consisting of TNF-αand TNF-β.

3. The method of claim 1 where the TNF inhibiting amount is from about a 1:300 dilution to a 1:600 dilution and the cell line is the HL-60 cell line or a derivative of the HL-60 cell line.

4. The method of claim 1 where the extract is selected from the group consisting of CM-4 and PCM-4.

* * * * *